(12) United States Patent
Vanoni et al.

(10) Patent No.: US 7,410,775 B2
(45) Date of Patent: Aug. 12, 2008

(54) METHOD FOR MAKING RECOMBINANT PEPTIDES OR PROTEINS USING SOLUBLE ENDOPROTEASES

(75) Inventors: Marco Vanoni, Monza (IT); Paolo Tortora, Milan (IT); Giancarlo Tonon, Milan (IT); Geoffrey Taylor, Milan (IT); Gaetano Orsini, Gallarate (IT)

(73) Assignee: Bio-Ker S.R.L., Gessate (IT)

( * ) Notice: Subject to any disclaimer, the term of this patent is extended or adjusted under 35 U.S.C. 154(b) by 0 days.

(21) Appl. No.: 11/804,557

(22) Filed: May 18, 2007

(65) Prior Publication Data

US 2007/0298457 A1 Dec. 27, 2007

Related U.S. Application Data

(62) Division of application No. 10/181,277, filed as application No. PCT/EP01/13257 on Nov. 14, 2001, now Pat. No. 7,241,609.

(30) Foreign Application Priority Data

Nov. 16, 2000 (IT) .......................... MI2000A2465

(51) Int. Cl.
C12P 21/06 (2006.01)
C12N 9/48 (2006.01)
(52) U.S. Cl. ..................................... 435/68.1; 435/212
(58) Field of Classification Search ........................ None
See application file for complete search history.

(56) References Cited

FOREIGN PATENT DOCUMENTS

EP 0327377 8/1989

OTHER PUBLICATIONS

Swiss-Prot Database Accession No. P09231, KEX1 protease precursor from *K. lactis*, Mar. 1, 1989.
D. Germain, et al., Expression of the *Saccharomyces cerevisiae* Kex2p endoprotease in insect cells, Eur. J. Biochem. 204, 121-126 (1992).

M. Wishart, et al., "A Single Mutation converts a Novel Phosphotyrosine BInding Domain into a *Dual-specificity* Phospatasse," *The Journal of Biological Chemistry*, Nov., 1995, vol. 270., No. 45, pp. 26782-26785.
A. Witkowski, et al., "Conversion of a β-Ketoacyl Synthase to a Malonyl Decarboxylase by Replacement of the Active-Site Cysteine with Glutamine," *Biochemistry*, 1999, 28, pp. 11643-11650.
J. Davey, et al., "Isolation and characterization of krp, a dibasic endopeptidase required for cell viability in the fission yeast *Schizosaccharomyces pombe*," *The EMBO Journal*, 1994, vol. 13, No. 24, pp. 5910-5921.
L. Lee, et al., "Molecular characterization of KEXI, a kexin-like protease in mouse *Pneumocystis carinii*," *Gene*, 2000, 242, pp. 141-150.
L. Latchinian-Sadek, et al., Secretion, purification and characterizatio of a soluble form of the yeast KEXI-encoded protein from insect-cell cultures, *Eur. J. Biochem*, 1994, 219, pp. 647-652.
C. Tanguy-Rougeau, et al., The *Kluyveromyces lactis* KEXI gene encodes a subtilisin-type serine proteinase, *Febs Letters*, Jul. 1998, Vo.. 234, No. 2, pp. 464-470.
J. Whisstock, et al., "Prediction of protein function from protein sequence and structure," *Quarterly Reviews of Biophysics*, 2003, vol. 306, No. 3, pp. 307-340.
R. Gayle, et al., "Identification of Regions in Interleukin 1α Important for Activity," *The Joumal of Biological Chemistry*, Oct., vol. 268, No. 29, pp. 22105-22111, 1988.
Tsugita et al., Developments in protein microsequencing, *Adv Biophys*., 1987, 23, pp. 81-113, Review.
Nedeva et al, Screening of thermotolerant yeasts as producers of superoxide dismutase., FEMS Microbiol Lett., Feb. 1993, , 107, pp. 49-52.
UniProt Database Accession No. P09231.
PIR_79 Database Accession No. KXBY from Mizuno et al Yeast KEX2 genes encodes an endopeptidase homologous to subtilisin-like serine proteases, Biohem Biophys Res Commun., Oct. 1988, 156(1), pp. 246-254, Alignment with Seq ID No. 2.
Issued Patents AA Database from US5,935,815 van den Ven et al. Mar. 8, 1999 Seq. ID No. 4, Alignment with Seq ID No. 2.

*Primary Examiner*—Sheridan Swope
(74) *Attorney, Agent, or Firm*—Darby & Darby P.C.

(57) ABSTRACT

The present invention relates to the expression and secretion in *Saccharomyces cerevisiae* of readily purifiable soluble variants of the Kex1 endopeptidase of *Kluyveromyces lactis* and the purification and use thereof for the in vitro processing of recombinant proteins usable in industrial applications. The soluble Kex1 endoproteases described here are free from the transmembrane domain of the native enzyme; the deletion of the transmembrane domain is achieved by removing at least 57 amino acid residues from the C-terminal.

5 Claims, 7 Drawing Sheets

Figure 2

METHOD FOR MAKING RECOMBINANT PEPTIDES OR PROTEINS USING SOLUBLE ENDOPROTEASES

CROSS REFERENCE TO PRIOR APPLICATION

This application is a Divisional of U.S. patent application Ser. No. 10/181,277 filed Jul. 11, 2002, now U.S. Pat. No. 7,241,609, which application is a U.S. national phase of International Application No. PCT/EP01/13257, filed Nov. 14, 2001, which application claims priority from Italian Application No. MI2000A002465, filed Nov. 16, 2000. The disclosure of all applications are incorporated herein by reference in their entirety.

The present invention relates to novel endopeptidases having a high cutting specificity to be used in the in vitro processing of recombinant proteins usable in industrial applications and, more particularly, soluble secreted derivatives of the Kex1 protein of *Kluyveromyces lactis* and the use thereof, in a soluble form or in a form immobilized on an insoluble organic or inorganic support, for the release of the protein of interest from fusion proteins.

FIELD OF THE INVENTION

The manufacture of heterologous recombinant proteins in suitable expression systems is one of the main applications of industrial interest of recombinant DNA technology. Owing to the instability of the peptide/protein in the host cell, it is often advantageous to manufacture the peptide/protein of interest in the form of a fusion protein comprising a protective (or stabilising) protein which will subsequently be processed at a specific predetermined site in order to free the desired protein or peptide.

That process also enables the desired protein or peptide to be obtained without the extension of an N-terminal methionine residue which constitutes the first amino acid residue of proteins expressed in bacterial systems. Fusion proteins are also manufactured with the aim of increasing expression levels or of facilitating the purification process by the selection of suitable polypeptide sequences, to the amino- or carboxy-terminal ends of which the protein of interest is attached.

The success of that strategy requires the availability of chemical or enzyme reagents that can effect the processing of the fusion protein with the desired level of specificity, ideally without releasing any secondary products, so as to reduce the cost of downstream processing. Of the chemical methods proposed, mention may be made of cutting at methionine residues with CNBr, acid hydrolysis at the Asn-Pro dipeptide or cutting with hydroxylamine at the Asn-Gly dipeptide (Fontana et al.; Practical protein chemistry. A handbook. pp. 5569-575, 1986). The enzyme methods make use, for example, of lysil-endopeptidases (Achromobacter protease I) which specifically cut the peptide bond from the carboxyl end of the lysine and protease V8 from *staphylococcus* which specifically cuts the peptide bond from the carboxyl end of glutamic acid (Japanese Examined Patent Publication No. 6-87788). However, because those chemical methods and the endoproteases recognise a single amino acid residue, it is necessary for the amino acid residue not to be present in the desired peptide in order to permit the efficient excision of the desired peptide from the chimeric protein; thus, the peptides that can be manufactured are limited. Various studies have therefore been directed to the search for and/or engineering of proteases having substrate specificity suitable for their use in the specific proteolytic cutting in vitro of recombinant proteins of industrial interest. Other endoproteases having a cutting sequence which is more restricted, that is to say, which covers a sequence of amino acids and not a single residue, have been used and include, for example, thrombin, factor Xa and enterokinase (Nilsson et al., Current Opinion Struct. Biol. 2, 569-575, 1992).

More recently, considerable interest has been concentrated on some members of the family of the subtilases, or serine proteases, the more well-known members of which are: (1) bacterial subtilysines, (2) the Kex2 protease of *S. cerevisiae*, (3) furine and furine-analogue proteins. In particular, while bacterial subtilysines do not exhibit sufficient cutting specificity for the in vitro processing of fusion proteins, except in suitably engineered variants (Ballinger et al., Biochemistry 35, 13579-13585, 1996; U.S. Pat. No. 5,837,516), both the Kex2 protein and furines exhibit a cutting specificity adequate for the purpose.

Subtilases having a high cutting specificity, which will be referred to hereinafter by the term kexino-analogue proteases, play the molecular/physiological role of "pro-hormone convertases"; that is to say, they are enzymes that produce peptide hormones from their precursors in vivo, by proteolytic cutting at the C-terminal end of pairs of base residues, Lys-Arg or Arg-Arg. FIG. 1 shows diagrammatically the structure of kexino-analogue proteases. The subtilysine-analogue catalytic domain which extends for approximately 330 amino acids is highly conserved between the eukaryotic pro-protein convertases. In particular, the residues of the active site which constitute the catalytic triad (Ser-His-Asp) and a residue of Asn which stabilises the oxyanionic cavity in the transition state, are present in corresponding positions in all members, except in PC2, where the Asn residue is substituted by an Asp residue (Bryan et al., *Proc. Natl. Acad. Sci. U.S.A.*, 83: 3743-3745 1986).

The sequences flanking those residues are also well conserved. In addition, the region of 140 amino acids which follows the catalytic domain, known as "Homo B", "P" or "middle" domain, is also well conserved between the eukaryotic convertases, including the yeast protease Kex2, but is absent from bacterial subtilysines. The Homo B domain is essential for catalytic activity (Zhong et al., *FEBS Lett.*, 396: 31-36. 1996). That domain contains a conserved Arg-Gly-Asp sequence which resembles the recognition sequence of integrins. The mutation of one of those three residues in PC1/PC3 causes the loss of catalytic activity and the incorrect directing of that neuroendocrine convertase towards the constituent secretive pathway (Lusson et al., *Biochem. J*, 326: 737-744 1997). Another conserved region is the propeptide, which is removed autocatalytically by processing the Arg-Xaa-Lys-Arg site during the maturing of the convertases. Towards the C-terminal end, furine, PACE4, PC5/PC6A and B have a domain rich in Cys, which is well conserved and the role of which has hitherto been unknown. Furine, Kex2, PC5/PC6B and LPC/PC7/PC8/SPC7 also have a transmembrane domain near the C-terminal end.

The Kex2 endoprotease of the yeast *Saccharomyces cerevisiae* was the first enzyme demonstrated, to which genetic and biochemical proofs have permitted the ascribing of the function of processing pro-proteins at di-base sites in the trans-Golgi network.

The KEX2 gene codes for a glycoprotein of 814 amino acid residues with a molecular mass of from 100 to 120 kDa. That glycoprotein is anchored to the membranes of the trans-Golgi network and has the physiological role of processing the α-factor and the killer toxin. The Kex2 protein is a calcium-dependent protease serine which specifically cuts peptide bonds at the C-terminal end of Lys-Arg, Arg-Arg and Pro-Arg sequences (Mizuno et al., *Biochem. Biophys. Res. Comm.*

144: 807-814 1987). The amino acid sequence of Kex2 contains, in the $NH_2$-terminal portion, a pre-pro-domain having potential autoproteolytic sites ($Lys_{79}$-$Arg_{80}$, $Pro_{102}$-$Arg_{103}$ and $Lys_{108}$-$Arg_{109}$) followed by a region (144-438 aa) having a high degree of sequence homology (identity of 30%) with bacterial subtilases (Mizuno et al., *Biochem. Biophys. Res. Commun.*, 156: 246-254 1988; Fuller et al., *Proc. Natl. Acad. Sci. USA*, 86: 1434-1438 1989). The Kex2 protease is expressed in the MATα cells of the yeast *S. cerevisiae* as an inactive precursor and the $NH_2$-terminal region of the mature form is generated by proteolytic processing at the $Lys_{108}$-$Arg_{109}$ site, followed by proteolytic cutting of the dipeptides Leu-Pro and Val-Pro by the dipeptidyl-aminopeptidase enzyme Ste13 (Brenner and Fuller, *Proc. Natl. Acad. Sci. USA*, 89: 922-926 1992).

The catalytically active Kex2 protease of *S. cerevisiae* was purified from yeast as a secreted soluble enzyme (ss-Kex2) generated by the insertion of a stop codon before the COOH-terminal transmembrane domain. This modification facilitated the purification of the enzyme. Studies on the substrate specificity of the purified ss-Kex2 *S. cerevisiae* protease have demonstrated that the protease does not exclude any residue in the P3 position except for Asp and Pro, but is, on the other hand, selective for amino acids in the P2 and P1 position. In particular, Kex2 in the P2 position would exclude amino acids having bulky chains, but would, however, recognise those having positively charged residues while, in the P1 position, the Kex2 endoprotease is extremely selective both for the charge and for the structure of arginine. EP-327377 describes Kex2 proteases of *S. cerevisiae* that are free from the C-terminal hydrophobic region; those proteases are soluble in water and can be secreted outside the cell, leaving the enzyme activity of the native protein unaltered.

BRIEF DESCRIPTION OF THE DRAWINGS

FIG. 2 shows the alignment of the protein sequences of Kex2 from *S. cerevisiae* (SEQ ID NO: 4) and Kex1 from *K. lactis* (SEQ ID NO: 3).

DETAILED DESCRIPTION OF THE INVENTION

Figure 1:
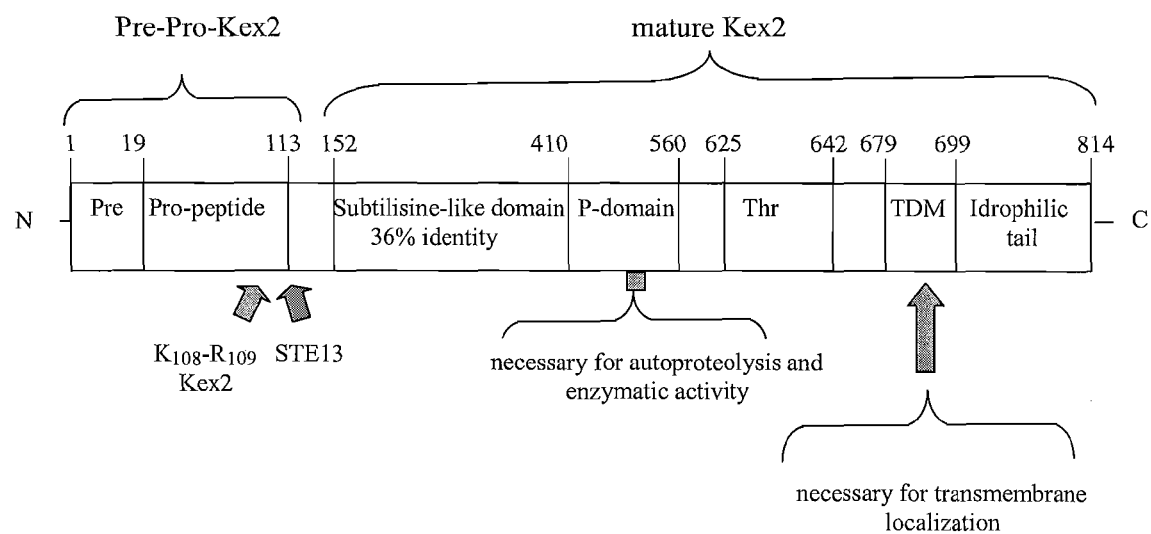
FIG. 1 shows the structural organisation in domains of the Kex2 protein, a typical representative and the first identified member of the family of the kexin-analogue processing subtilases.

Some strains of *Kluyveromyces lactis* exhibit a killer phenotype secreting a toxin capable of killing sensitive cells of various species of yeast. That killer property is due to the presence of two plasmids of linear DNA, pGKL1 and pGKL2, which cooperate to produce the toxin and a component which permits the immunity thereof. A mutation (kex1) was isolated at a single locus of the *K. lactis* chromosome, called KEX1, which mutation leads to the loss of the killer phenotype, while enabling the above-mentioned plasmids to be maintained.

Cloned by genetic complementation of the above-mentioned mutation, the gene KEX1 was found to be orthologous to the gene KEX2 of *Saccharomyces cerevisiae*. The proteins encoded by the genes KEX2 of *S. cerevisiae* and KEX1 of *K. lactis* have a high degree of sequence homology (identity >50%) and each of them is capable of compensating for the deficiency of the other. That information suggests that the KEX1 gene of *Kluyveromyces lactis* (Wesolowski-Louvel et al. *Yeast* 4: 71-81 1988) codes also for a protease that has cutting specificity for di-base residues and that is involved in the production of the mature form of the killer toxin generated by processing its precursor. However, hitherto no data have been available relating to the expression of the product of the KEX1 gene, nor have any data been available concerning the biochemical and enzymatic characterisation of that protein.

Recombinant Kex1 proteases of *K. Lactis*, constituting the principal object of the present invention, have now been found that are free from the transmembrane domain (and will be referred to by the term ss-Kex1) and that manifest in vitro endopeptidase catalytic activity in respect of substrates containing Pro-Arg residues and di-base residues, in particular, towards Arg-Arg, Lys-Arg residues.

It has also surprisingly been found that those recombinant Kex1 proteases, the protein sequence of which, except for deletions comprising the domain for anchoring to the membrane (possibly except for deletions comprising the domain for anchoring to the membrane) corresponds to that encoded by the KEX1 gene of *K. Lactis*, demonstrate substantially greater thermal stability compared with proteins of the same family, the protein sequence of which corresponds to that encoded by the KEX2 gene of *S. cerevisiae*, so that they can be used in processes of targeted proteolysis in vitro under conditions in which other proteins of the kexine family, in particular Kex2 from *S. cerevisiae*, are inactivated.

The soluble Kex1 proteases according to the present invention are characterised by a greater stability compared with the corresponding variants encoded by the KEX2 gene of *S. cerevisiae*, the soluble Kex1 proteases preserving more than 50% of their activity under conditions in which the Kex2 protein is completely inactivated.

As will be appreciated from the following, in the soluble Kex1 endoproteases according to the present invention, the deletion of the transmembrane domain is achieved by removing at least 57 amino acid residues from the C-terminal of the enzyme encoded by the KEX1 gene of *K. lactis*; in the preferred embodiment of the invention, at least 57 and not more than 100 amino acid residues are removed from the C-terminal; the gene sequence used experimentally is that available from the EMBL data bank under the accession number X07038.

In particular, the soluble Kex1 endoprotease according to the preferred embodiment of the present invention is characterized by having sequence SEQ ID NO 2 or, in any case, by having a sequence with a 90% homology, preferably a 95% homology, with respect to SEQ ID NO 2.

A second object of the present invention is represented by a DNA molecule coding for a soluble Kex1 endoprotease according to the present invention and, in particular, coding for a soluble Kex1 endoprotease in which at least 57 amino acid residues have been removed from the C-terminal and, preferably, coding for a soluble Kex1 endoprotease in which at least 57 and not more than 100 amino acid residues have been removed from the C-terminal.

According to a preferred embodiment said DNA molecule is characterized by (a) having sequence SEQ ID NO 1, (b) having a sequence which hybridize to SEQ ID NO 1, (c) having a sequence which is degenerate as a result of the genetic code to the DNA having sequence SEQ ID NO 1 and/or (d) having a sequence with a 90% homology, preferably a 95% homology, with respect to SEQ ID NO 1.

A further object of the invention is constituted by a process for the manufacture of a biologically active substance of interest (a peptide or a protein), comprising:
(a) the production of a fusion polypeptide or protein comprising the sequence of the peptide or protein of interest in a construct of the type $NH_2$—A—B—C—COOH, where $NH_2$ is the $NH_2$-terminal end of the fusion polypeptide or protein, A is any desired protein or polypeptide (optionally only the methionine encoded by the start codon of the translation), B is a joining "linker" fragment terminating with an amino acid sequence recognised by the Kex1 endoprotease of the present invention, C represents the polypeptide or protein of interest, so that the first amino acid of the mature protein of interest is immediately at the carboxyl end of the sequence recognised by the Kex1 endopeptidase according to the present invention and COOH represents the carboxy-terminal end of the fusion polypeptide or protein;
(b) the in vitro incubation of the fusion polypeptide or protein mentioned in step (a) above in the presence of a Kex1 endoprotease according to the present invention, in order to separate the protein or polypeptide of interest from the fusion partner and with the free $NH_2$-terminal end corresponding to the $NH_2$ terminal end of the polypeptide or protein of interest;
(c) the separation and purification of the biologically active peptide or protein of interest.

The procedures for carrying out operations (a), (b) and (c) listed above are well known in the art and therefore do not have to be explained in detail; they are described, for example, in documents EP-327377, EP-794254, EP-794255 and U.S. Pat. No. 5,077,204, the content of which is to be regarded as an integral part of the present description.

The endoproteases according to the present invention can be used to process fusion proteins containing peptides or proteins of industrial and/or therapeutic interest; possible proteins obtainable using the process according to the present invention are, for example, recombinant proteins for therapeutic use, such as, for example, peptide hormones, interleukins, interferons, cytokines, growth factors, fibrinolytic enzymes and recombinant enzymes of industrial interest which can be used as biocatalysts, such as, for example, lipases, hydrolases, nucleases, oxidases, phosphatases.

Other objects of the invention are represented by the DNA sequences which code for the above-mentioned proteases, by the corresponding expression plasmids and by the host cells containing them.

The Kex1 protease of *Kluyveromyces lactis* according to the present invention was obtained by causing variants of the Kex1 protease that are free from the domain for anchoring to the membrane to be expressed in the *Saccharomyces cerevisiae* yeast. The secretion in the growth medium of the ss-Kex1 proteases was achieved either by means of the homologous pre-pro region or by means of the pre-pro region of the homologous Kex2 protein of *S. cerevisiae*, as well as thanks to the (pre) signal sequence of the glucoamylase of *Saccharomyces cerevisiae* var. *diastaticus*. Owing to those studies, it was surprisingly found that the catalytic domains of Kex1 and Kex2 have functional differences as demonstrated by the observation that the Kex1 protein terminating at residue 580 is catalytically inactive, unlike the Kex2 protein terminating at residue 593, which is the corresponding residue in the Kex2 protein (Gluschankof et al., *EMBO J.*, 13: 2280-2288 1994). Growth conditions more suitable for the production and secretion of the protease in a flask were also sought.

Soluble Kex1's were purified from the growth medium and some of their biochemical properties were determined, including the cutting efficiency on model substrates and the stability and catalytic activity in the presence of various physico-chemical agents, such as the temperature.

The ss-Kex1 proteases so obtained can be used as such or can be immobilised on an insoluble organic or inorganic matrix; the proteases so immobilised can be reused several times in the in vitro processing of fusion proteins of industrial interest, with evident advantages.

The thermal stability of the novel soluble secreted ss-Kex1 endopeptidases is such that they maintain approximately 60% or more of their original activity after incubation at 50° C. for 6 minutes, under which condition the corresponding Kex2 proteins lose their activity completely.

The estimated molecular mass of the novel ss-Kex1 endopeptidases of the present invention is approximately from 65 to 70 kDa (enzyme produced from the strain NP31) and from 70 to 80 kDa (enzyme produced from the strain NP168) as determined in SDS-PAGE after heating and reduction of the sample.

The invention will be explained hereinafter by specific examples. The examples have the sole purpose of clarifying the invention, although it should be appreciated that the invention is not in any way limited thereby.

EXAMPLES

Example 1

Construction of Plasmids for the Expression of Kex1 from *Kluyveromyces lactis* in *Saccharomyces cerevisiae*

Unless otherwise indicated, conventional procedures were used for all the standard manipulations of the recombinant DNA. A collection of those procedures is given, for example, in Sambrook et al., (1989) Molecular Cloning.

In order to construct plasmids for the expression in *S. cerevisiae* of truncated variants of the COOH-terminal region of the Kex1 protease of *K. lactis*, under the control of various signal sequences, PCR's were carried out with suitable mutagenic oligonucleotides, standard subcloning procedures being followed. The expression vectors used in this invention were pEMBLyex4 (Baldari et al, *EMBO J.*, 6: 229-234 1987), pVTU (Vernet et al., *Gene* 52: 225-233 1987) and YEPSTA (Martegani et al., *Appl. Microbiol. Biotechnol.*, 37: 604-608 1992).

Figure 2:
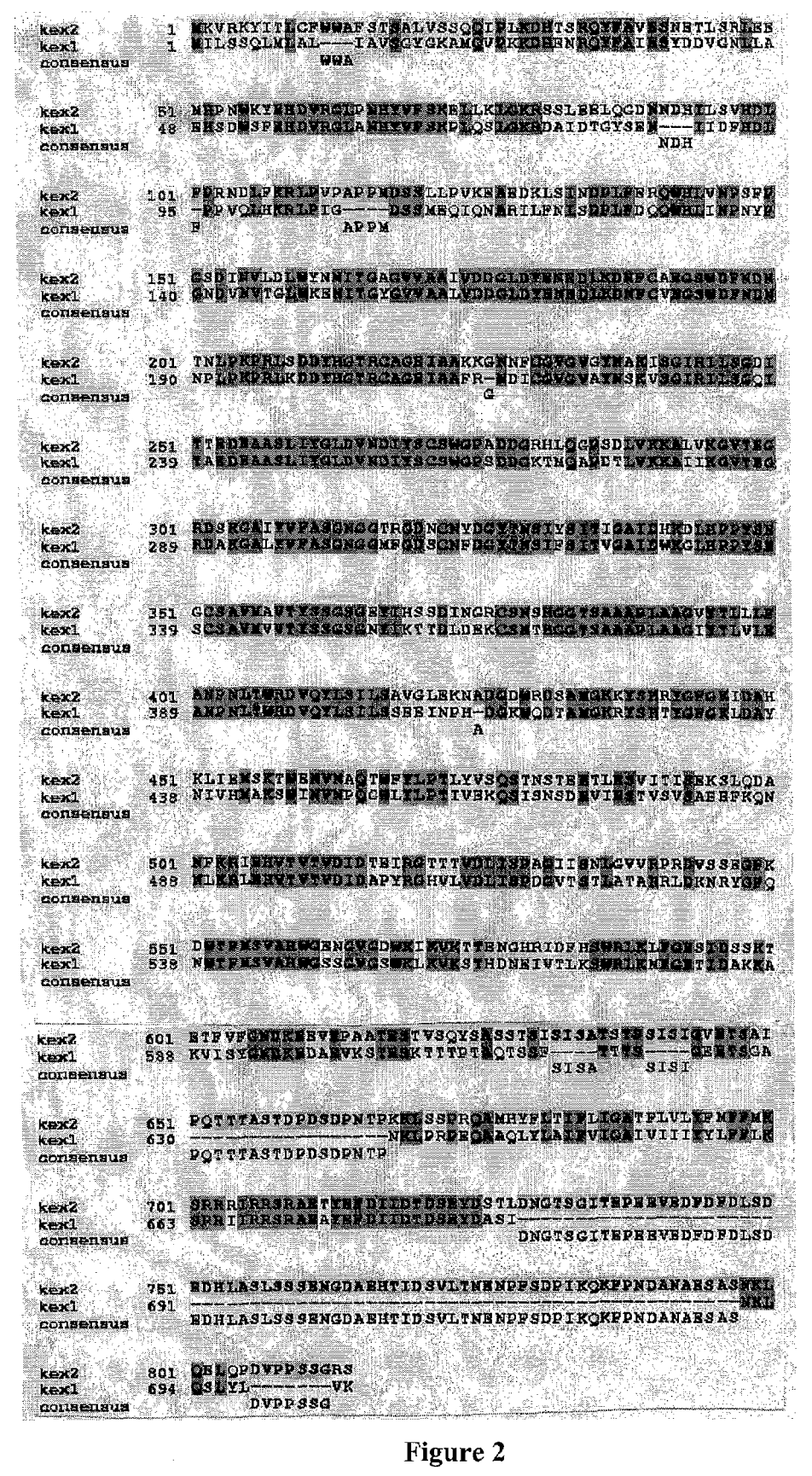

The plasmids expressing kexines from those derivatives are listed in Table 1. On the basis of the information given in that Table, it will be possible for experts in the art to construct the above-mentioned plasmids without excessive experimentation. In this patent, reference is made to the following sequences of proteins and nucleic acids: (KEX1 gene, EMBL accession number X0738; Kex1 protein, Swiss-Prot accession number 09231; KEX2 gene EMBL accession number M22870; Kex2 protein, Swiss-Prot accession number P13134). In the following text, nucleotide 1 refers to the adenine nucleotide (A) corresponding to the translation start codon (ATG) of each given gene coding for proteases; similarly, amino acid 1 refers to the methionine encoded by said start codon. Analogously to the description given above for Kex2, the soluble and enzymatically active mature forms of Kex1 described in the present invention are initially expressed in the form of inactive pre-pro-proteins which are subsequently processed at the Lys101-Arg102 site (when the homologous pro-protein is used) or at the Lys-113-Arg-114 site (when the kex2 pro-protein is used). For the purposes of the present invention, the soluble and enzymatically active mature forms of Kex1 are characterised by having a polypeptide chain between amino acid 103 and amino acid 643 of the sequence given in FIG. 2 and are indicated by ss-Kex1-Cx terminology, where x represents the amino acid residue of the sequence of FIG. 2 which constitutes the carboxy-terminal residue of the soluble forms of Kex1. Purely by way of example, the construction of the PL24 plasmid which expresses the Kex1-C600 protease is given in detail. Since the DNA sequences are known, the construction of those plasmids is within the ordinary competence of an expert in the art and can also be carried out by means of strategies and techniques which differ from those exemplified but which are equivalent in terms of obtaining the expected product(s).

In order to construct the plasmid for the expression of the Kex1-C600 truncated at amino acid 600, which residue corresponds to amino acid 613 in the Kex2 protein encoded by the KEX2 gene of *S. cerevisiae*, the sequence encoding residues 1-600 of Kex1 was amplified by means of PCR with the oligonucleotides indicated below (the nucleotides constituting the restriction sites for BamHI and HindIII are underlined):

5'CGC GGA TCC ATG ATC CTA TCG TCG CAG C3'

5'C CCC AAG CTT TCA TTC AGC ATC CTC TTT GTC3'

At the end of the PCR, the amplified fragment was subjected to restriction with the endonucleases BamHI and HindIII, purified from agarose gel after preparative electrophoresis and subcloned in the expression vector pEMBLyex4 which had been linearised beforehand with BamHI and HindIII, thus allowing plasmid pL24 to be obtained which enables the Kex1-C600 protein to be expressed in yeast under the control of the inducible hybrid promoter GAL1-10-CYC1.

Example 2

Expression and Secretion of the Kex1 Protein of *Kluyveromyces lactis* in *Saccharomyces cerevisiae*

Various strains of *S. Cerevisiae* were transformed using the constructs described above in order to obtain the expression of catalytically active and soluble secreted forms of the Kex1 protease of *K. Lactis*. GRF18* (MATαhis 3-11, 15 leu 2-3, 112 ura3); X4004 (MATαlys5 met2 ura3 trp1); MVY4935 (MATαsta10 leu2 ura3 arg4 his3 lys2); W303 1-a (MATαleu2-3,112 ura3-1 trp1-1 his3-11,15 ade2-1 can1-100 GAL SUC2). The method of transformation used is that described in Schiestl and Gietz (1989) *Curr. Genet.* 16: 339-246. The flasks used for growing the yeast in liquid medium were incubated in a Dubnoff thermostated bath and agitated continuously. Growth on a plate was carried out in suitable incubators in a humid atmosphere. For the methodology in respect of the yeast, wherever the methods are not explicitly described, reference should be made to C. Guthrie and G. R. Fink, Methods in Enzymology 194.

The transformed cells were plated onto selective minimum medium (YNB), with glucose as the source of carbon, and were incubated at 30° C. Under those conditions, the engineered cells grow without producing the protein of interest. The expression system based on the pEMBLyex4-analogue vectors can be induced by galactose, because the protein of interest is placed under the control of the inducible hybrid promoter GAL-CYC, and the presence of glucose in the culture medium brings about a state of repression of the expression. That system provides for the use of raffinose as the source of carbon for permitting the de-repression and the use of galactose in order to ensure the induction state. In addition, the expression system based on pEMBLyex4-analogue vectors provided with the selective marker leu2d provides the possibility of further amplifying the number of copies of the plasmid of interest, having recourse, when permitted by the genotype of the transformed strain, to selection in minimum medium free from leucine.

The transformed strains were grown in the following culture media:

YP-rich medium: Source of carbon 20 g/l; Peptone 20 g/l; Yeast extract 10 g/l.

TABLE 1

Plasmids used in this invention expressing various forms of kex1

| Plasmid | Marker(s) | Parent plasmid | Promoter | Pre sequence | Pro sequence | ss-Kex1-Cx |
|---------|-----------|----------------|----------|--------------|--------------|------------|
| PL24 | URA3, leu2d | pEMBLyeex4 | GAL10-CYC1 | $Kex1_{1-24}$ | $Kex1_{25-102}$ | Kex1-C600 |
| PL57 | URA3, leu2d | pEMBLyeex4 | GAL10-CYC1 | $Kex1_{1-24}$ | $Kex1_{25-102}$ | Kex1-C579 |
| PL58 | URA3, leu2d | pEMBLyeex4 | GAL10-CYC1 | $Kex1_{1-24}$ | $Kex1_{25-102}$ | Kex1-C580 |
| PL98 | URA3, leu2d | pEMBLyeex4 | GAL10-CYC1 | $Kex1_{1-24}$ | $Kex1_{25-102}$ | Kex1-C611 |
| PL99 | URA3, leu2d | pEMBLyeex4 | GAL10-CYC1 | $Kex1_{1-24}$ | $Kex1_{25-102}$ | Kex1-C622 |
| PL86 | URA3, leu2d | pEMBLyeex4 | GAL10-CYC1 | $Kex1_{1-24}$ | $Kex1_{25-102}$ | Kex1-C640 |
| PL87 | URA3, leu2d | pEMBLyeex4 | GAL10-CYC1 | $Kex1_{1-24}$ | $Kex1_{25-102}$ | Kex1-C643 |
| PL120 | URA3, leu2d | pEMBLyeex4 | GAL10-CYC1 | $Kex2_{1-27}$ | $Kex2_{28-114}$ | Kex1-C600 |
| PL68 | URA3, leu2d | pEMBLyeex4 | GAL10-CYC1 | $Kex2_{1-27}$ | $Kex1_{25-102}$ | Kex1-C600 |
| PL22 | URA3, leu2d | YEpSTA | GAL10-CYC1 | $Sta2_{1-42}$ | $Kex1_{25-102}$ | Kex1-C600 |
| PL132 | URA3, leu2d | pEMBLyeex4 | GAL10-CYC1 | $Kex2_{1-27}$ | $Kex2_{28-114}$ | Kex1-C611 |
| PL133 | URA3, leu2d | pEMBLyeex4 | GAL10-CYC1 | $Kex2_{1-27}$ | $Kex2_{28-114}$ | Kex1-C640 |
| PL134 | URA3, leu2d | pEMBLyeex4 | GAL10-CYC1 | $Kex2_{1-27}$ | $Kex2_{28-114}$ | Kex1-C643 |
| PL135 | URA3 | PVTU | TDH3 | $Kex1_{1-24}$ | $Kex1_{25-102}$ | Kex1-C600 |
| PL144 | URA3 | pVTU | TDH3 | $Kex2_{1-27}$ | $Kex2_{28-114}$ | Kex1-C600 |

YNB-aa minimum medium: Source of carbon 20 g/l; YNB without amino acids 6.7 g/l.

Standard 1040 medium: YNB without amino acids and without ammonium sulphate 1.7 g/l; $(NH_4)_2SO_4$ 1.32 g/l; $NH_4Cl$ 5.0 g/l; BIS-TRIS 8.37 g/l; Source of carbon 20 g/l; L-tryptophan 0.12 g/l; Adenine-HCl 0.24 g/l; casamino acids 5.0 g/l. When required, the media were solidified with 2% Agar. Nucleotide bases and amino acids are added to 50 mg/l.

The culture medium of those transformed strains was subjected to activity measurement to prove the presence of a catalytically active secreted form of the protease of interest. The enzyme activity was determined by a calorimetric test which exploits the capacity of the enzyme to hydrolyse the substrate Z-L-tyrosine-L-lysine-L-arginine-p-nitroanilide (Z-Y-K-R-pNA). The incubation mixture comprises 0.1 mM Z-Y-K-R-pNA in 0.2 M Hepes, pH 7.0 and 1 mM $CaCl_2$, in a total volume of 1.5 ml at 37° C. The reaction is monitored at 405 nm, a wavelength at which the maximum decrease in the molar extinction coefficient (As), equal to $10.9$ $mM^{-1}$ $cm^{-1}$, occurs. An enzyme unit is defined as being the quantity of enzyme that catalyses the transformation of 1 µmole of substrate per minute under the conditions described above. Unless expressly indicated otherwise, the data presented in Table 2 refer to the activity secreted in the growth medium by derivatives of the W303 strain which was grown in a flask at 30° C., with agitation (220 rpm), in 1040 medium-2% galactose (except for strains NP255 and NP265 in which the carbon source added to the growth medium was 2% glucose). Various samples were taken along the growth curve for each strain. Table 2 gives the maximum activity measured for each transformed strain. As can be seen, good levels of secretion are observed both when the expression of Kex1 is guided by the GAL10-CYC1 promoter and when using the promoter of the dehydrogenase alcohol. The invention is therefore not limited by the type of promoter used, as long as the levels of secretion of the endoprotease of the invention are satisfactory.

TABLE 2

Maximum Kex1 activity secreted in the growth medium in a flask by strains of *S. cerevisiae* transformed with plasmids expressing various forms of the Kex1 protease of *K. lactis*

| Name of the transformed strain | Expression plasmid | Activity (mU/ml) |
| --- | --- | --- |
| NP31 | PL24 | 1300 |
| NP113 | PL57 | Not detectable |
| NP115 | PL58 | Not detectable |
| NP180 | PL98 | 960 |
| NP183 | PL99 | 1260 |
| NP166 | PL86 | 1250 |
| NP168 | PL87 | 1200 |
| NP231 | PL120 | 1230 |
| NP157 | PL68 | 700 |
| NP33 | PL22 | <120 |
| NP250 | PL132 | 1300 |
| NP251 | PL133 | 1250 |
| PL252 | PL134 | 1280 |
| NP255 | PL135 | 1290 |
| NP265 | PL144 | 1270 |

It was found that the replacement of the pre-pro sequence of Kex1 by that of Kex2 resulted in a protein which was secreted in the growth medium just as well as the Kex1 protein which used its own pre-pro sequence. Conversely, the replacement of the pre sequence alone (signal sequence) by the signal sequence of the glucoamylase encoded by the STA2 gene of *Saccharomyces cerevisiae* var. *diastaticus* (strain NP33) or the signal sequence of Kex2 (strain NP157) resulted in reduced secretion of the Kex1 protein. In the experiments described in the following Examples, use was therefore made of the protein whose secretion was guided by the pre-pro sequence of Kex1 or Kex2 (strains NP31 and NP231, respectively).

Figure 3:
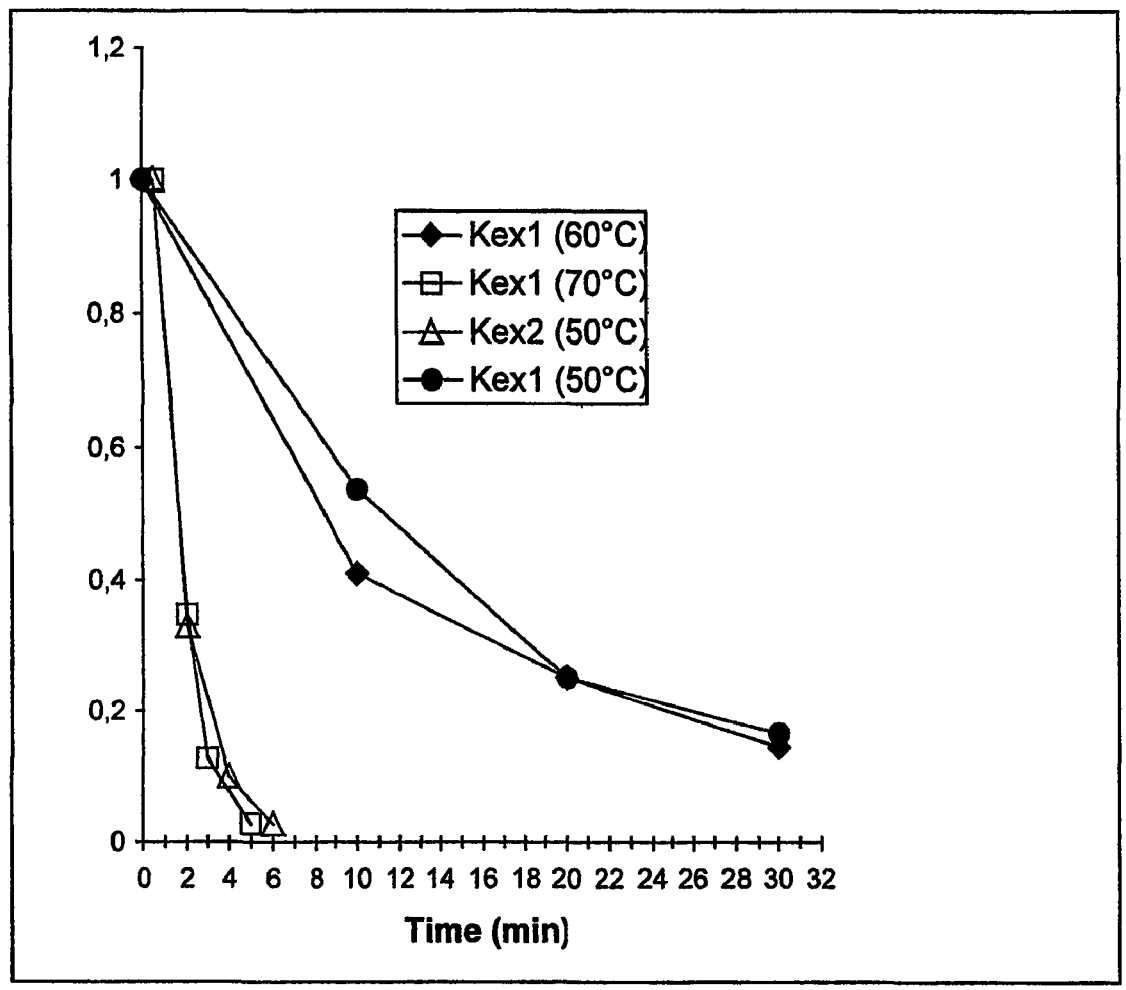
FIG. 3 shows the differences in thermal stability of the proteases ss-Kex2 from *S. cerevisiae* and ss-Kex1 from *K. lactis*.

It was surprisingly found that the strain NP115, expressing a Kex1 which terminates at amino acid 580, does not exhibit detectable enzyme activity. This result contrasts with the maintenance of enzyme activity on the part of the Kex2 protein which terminates at amino acid 593, that is to say, the amino acid of Kex2 corresponding to amino acid 580 of Kex1 of *K. lactis* (Gluschankof et al., supra, see also FIG. 2 for the alignments). This result means that, despite the high level of homology, the proteins Kex1 of *K. lactis* and Kex2 of *S. cerevisiae* differ considerably from one another so that they cannot be regarded as equivalents in all aspects relating to the embodiments of this invention. In this connection, account should also be taken of the comparative thermal stability data and activity profiles as a function of the temperature, which are given in FIGS. 3 and 4, respectively. Compared with the protein present in strain NP31, strains NP180, NP183, NP166 and NP168 have carboxy-terminal extensions which are able to cover the entire domain rich in serine/threonine, stopping immediately before the transmembrane domain. No significant differences compared with strain NP31 are observed in the Kex1 activity secreted in the growth medium by the above-mentioned strains.

Example 3

Figure 5:
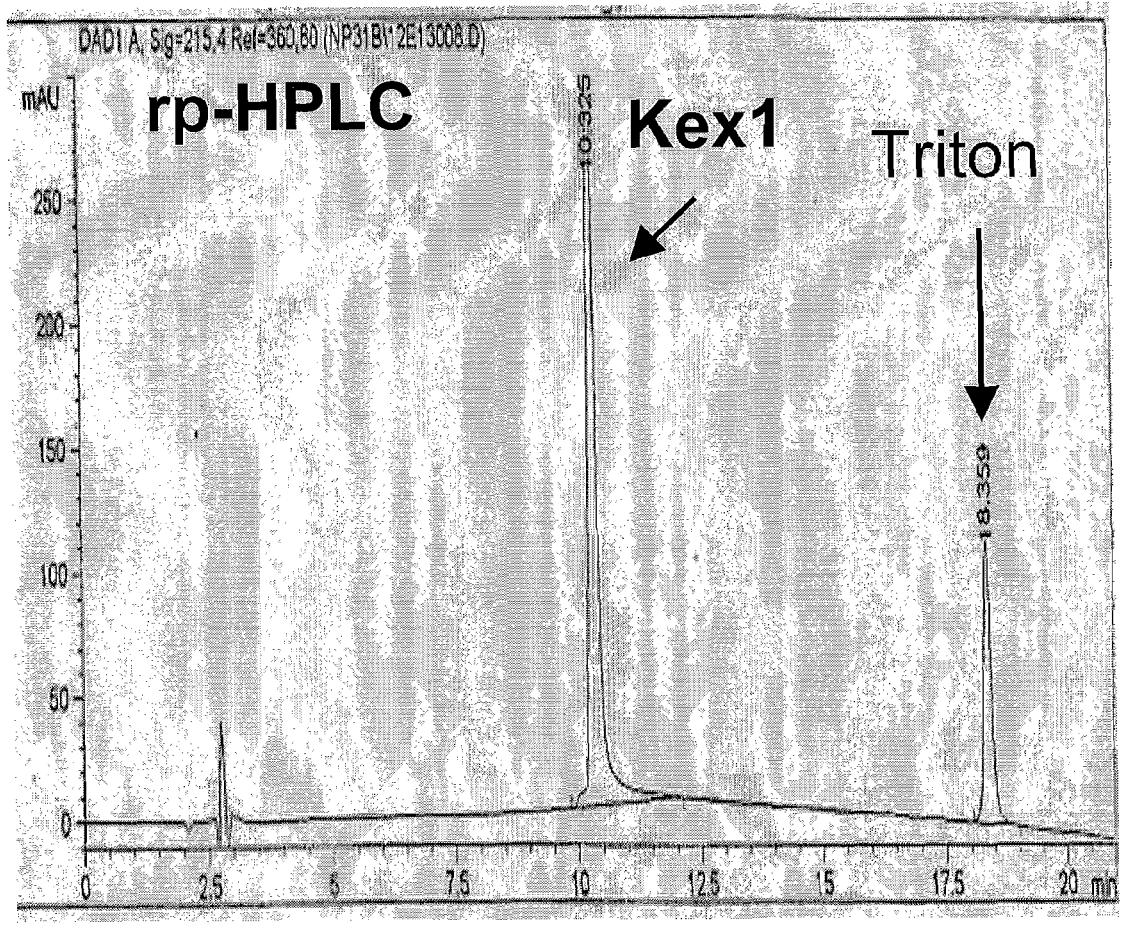
FIG. 5 shows the elution profile in RP-HPLC of a purified preparation of a soluble ss-Kex1 protease of the present invention.

Purification of the Kex1 Protein of *Kluyveromyces lactis* Secreted in the Growth Medium by Suitably Transformed *Saccharomyces cerevisiae* Strains The purification of the deleted variant of the Kex1 protease of *K. lactis* ss-Kex1-C600 was carried out starting from transformed strains of *S. cerevisiae* grown in a flask or in a fermenter up to the late exponential phase. In both cases, the medium was separated from the cells by centrifugation, filtered over a filter having 5 µm pores and then concentrated approximately 10 times and dialysed against a solution of Triton X-100 0.1%-$CaCl_2$ 4 mM by ultrafiltration on a membrane with cut-off at 10 kDa. The dialysed solution was purified on a column of SP-Sepharose resin pre-equilibrated with a sodium acetate buffer pH 5.2 and eluted by means of a linear gradient of pH in tris-acetate buffer. The fractions containing the enzyme activity of kex1 were introduced onto a column of Q-Sepharose resin pre-equilibrated with bis-tris-acetate buffer and were eluted by means of a linear gradient of NaCl. The pool of fractions containing the enzyme activity of kex1 was analysed by RP-HPLC. The RP-HPLC analysis was carried out using a Vydac-C18 column, 2.1×250 mm, at a temperature of 55° C. and with UV detection at a wavelength of 215 nm; the elution was carried out with a flow of 0.21 ml/minute starting from the mobile phases A (0.1% trifluoroacetic acid in water) and B (0.08% trifluoroacetic acid in acetonitrile) with a linear gradient from 37% to 87% of mobile phase B in 21 minutes. The analysis demonstrated the presence of a homogeneous peak with a purity of more than 95% (FIG. 5) and a specific activity of approximately 100 U/mg.

Example 4

Characterisation of the Kex1 Protein of *Kluyveromyces lactis*

The kinetic constants were determined by a simplified procedure which requires that measurements be carried out at a single initial concentration of substrate and until the substrate is exhausted. The method provides that, at various times, the average values of residual concentration and rate be determined and is applicable in those cases in which the enzyme catalyses an entirely irreversible reaction under the operating conditions, and is not subject to inhibition by product (Segel, I. H. (1975) Enzyme Kinetics, Wiley, New York). The results so obtained were processed using the Grafit programme, which permitted the interpolation of the Michaelis-Menten profile and the determination of the values of $K_m$ and $V_{max}$, presented in Table 3. $k_{cat}$ and the $k_{cat}/K_m$ ratio were then obtained from those values and from the enzyme concentration. The results show that the two proteases ss-Kex1 and ss-Kex2 do not differ significantly in their kinetic properties.

TABLE 3

Kinetic constants of the endoproteases ss-Kex2-C613 and ss-Kex1-C600

| | Vmax ($\Delta A\ min^{-1}) \times 10^3$ | $K_M$ µM | kcat $min^{-1}$ | kcat/$K_M$ $\mu M^{-1} \times min^{-1}$ |
|---|---|---|---|---|
| ss-Kex1-C600 | 1720 | 61.4 | $1.84 \times 10^5$ | $3.0 \times 10^3$ |
| ss-Kex2-C613 | 1029 | 56.8 | $1.37 \times 10^5$ | $12.4 \times 10^3$ |

Of the main characteristics of an enzyme which are required for industrial application as a biocatalyst, stability under operating conditions is definitely one of the most important. It will therefore be appreciated that it is necessary to investigate and characterise the two proteases from that point of view also. We initially determined the profile of thermal inactivation of the two enzymes at various temperatures in the absence of any stabilising agent. The profile was obtained by incubating the enzyme at the predetermined temperature, taking samples at successive times and determining the residual enzyme activity in the samples. The decline in the activity as a function of time, which activity is assumed to be proportional to the concentration of active enzyme, is thus determined.

Figure 4:
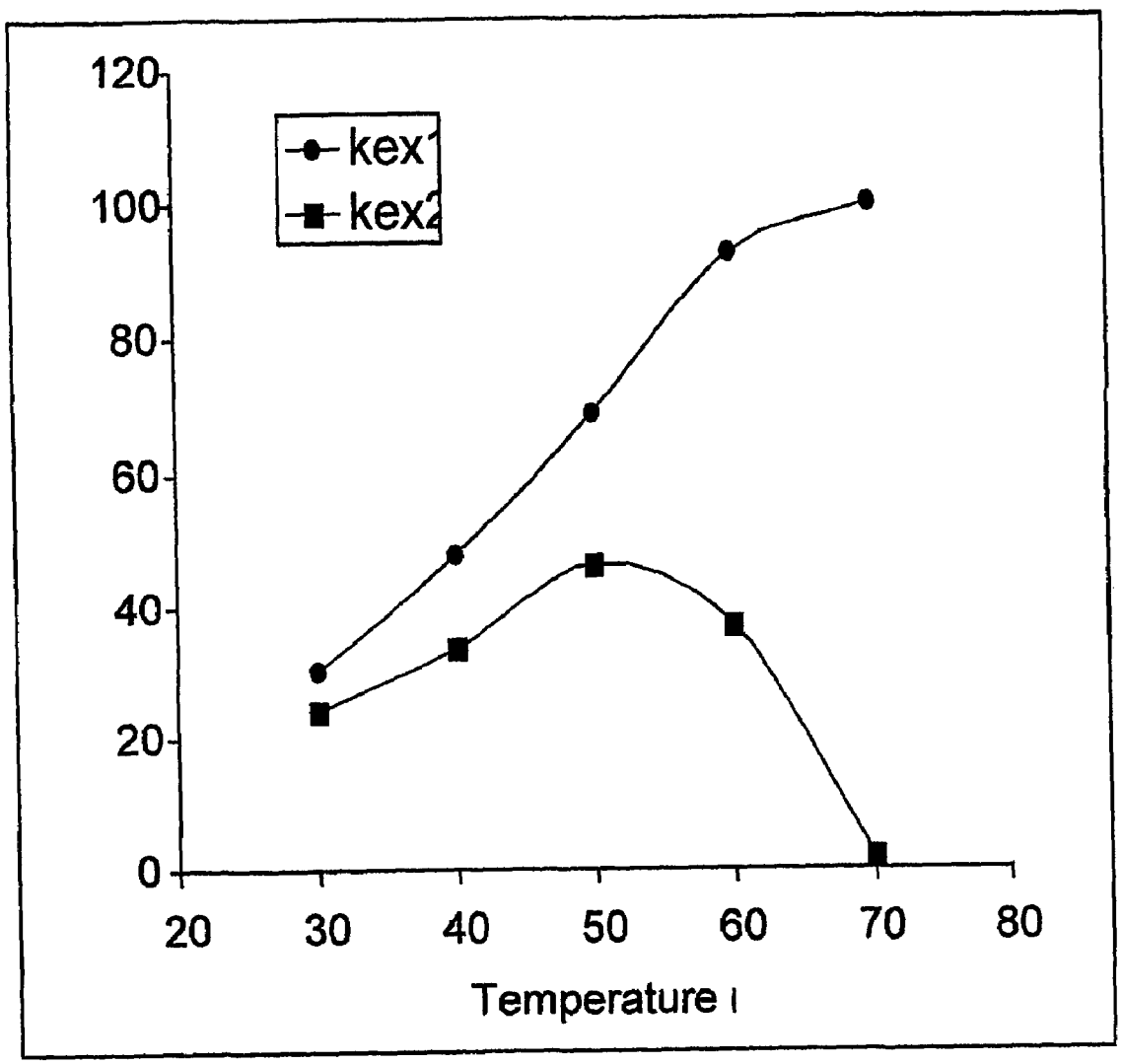
FIG. 4 shows the activity profile, including the optimum functioning temperature of the proteases ss-Kex2 from *S. cerevisiae* and ss-Kex1 from *K. lactis*.

The inactivation profiles of the two proteases were effected at temperatures of from 10 to 70° C. The data are given in FIG. 3 and show that, surprisingly, the ss-Kex1 protease has a thermal stability significantly higher than that of the ss-Kex2 protease: by way of example, the latter was almost completely inactivated after 6 minutes' incubation at 50° C. while, under the same conditions, Kex1 maintained not less than 50% of its activity. The inactivation profiles of the Kex1 protease at 60° C. and 70° C. and, for comparison, that of Kex2 at 50° C., also show the substantial difference in thermostability between the two molecules: it is clear that the ss-Kex1 protease is approximately as stable at 70° C. as the ss-Kex2 protein at 50° C., When ss-Kex1 and ss-Kex2 were dosed under standard conditions, with saturating concentrations of substrate and by measuring the average rate in the first 5 minutes of the reaction, the Kex1 protein exhibited an optimum functioning temperature of approximately 70° C. while, under the same conditions, the apparent optimum working temperature of the Kex2 endopeptidase was approximately 50° C. (FIG. 4).

Example 5

Figure 6:
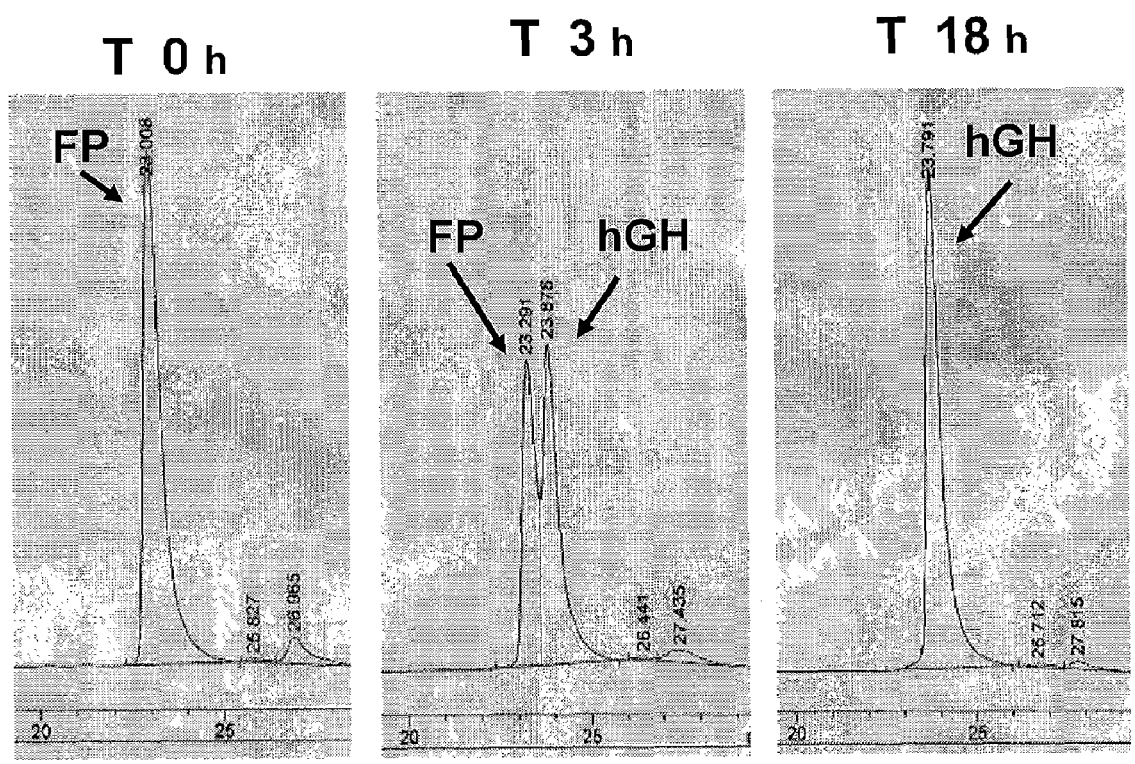
FIG. 6 shows the in vitro digestion kinetics of a fusion protein showing a reaction yield higher than 95% obtained with a soluble ss-Kex1 protease of the present invention.

Use of the Kex1 Protein of *Kluyveromyces lactis* in the Processing of Fusion Proteins The processing of fusion proteins was studied using, as a model protein, a fusion between a peptide sequence of 35 amino acids carrying the Lys-Arg dipeptide at the carboxy-terminal end and the sequence of 191 amino acid residues of the human growth hormone (h-GH). The fusion protein, having a structure (peptide portion)-(Lys-Arg)-(h-GH), had been expressed in a transformed strain of *E. coli*, extracted and purified to a degree of purity higher than 70%. The hydrolysis of the fusion protein (1 gram/liter) was carried out for a total period of 18 hours, in buffer at pH 7 containing 4 mM $Ca^{2+}$, at a temperature of 30° C. and using 0.2 mg/liter of a purified ss-Kex1-C600 preparation. The progress of the reaction was monitored by RP-HPLC analysis which showed a reaction yield higher than 95% (FIG. 6); the specificity of the hydrolysis was checked by analysis of the $NH_2$-terminal sequence of the reaction product which gave the expected sequence for h-GH. Similar results were obtained when h-GH was fused to polypeptides of different length (from 20 to 300 amino acid residues).

Example 6

Immobilisation of the Kex1 Protease and its Use in the Processing of Fusion Proteins The ss-Kex1 protease was immobilised using, as the inorganic solid support, the Eupergit C250L resin, the epoxy groups of which act as reactive groups for the formation of covalent bonds with the amino, thiol or hydroxyl groups of the enzyme. That reduces the structural flexibility of the enzyme and should therefore promote the stabilisation thereof. The incubation mixture comprises 780 µg of enzyme in 1 M potassium phosphate buffer, pH 7.0 in the presence of 8 mg of Eupergit C250L resin, in a total volume of 55 µl at ambient temperature for 4 days, without agitation. At the end of the incubation period, the immobilised enzyme is subjected to successive washing operations with the dosage buffer Hepes 0.2 M pH 7.0+$CaCl_2$ 1 mM, and is preserved at 4° C. in the presence of a solution of 0.2 M Hepes, pH 7.0, 1 mM $CaCl_2$/60% glycerol.

Figure 7:
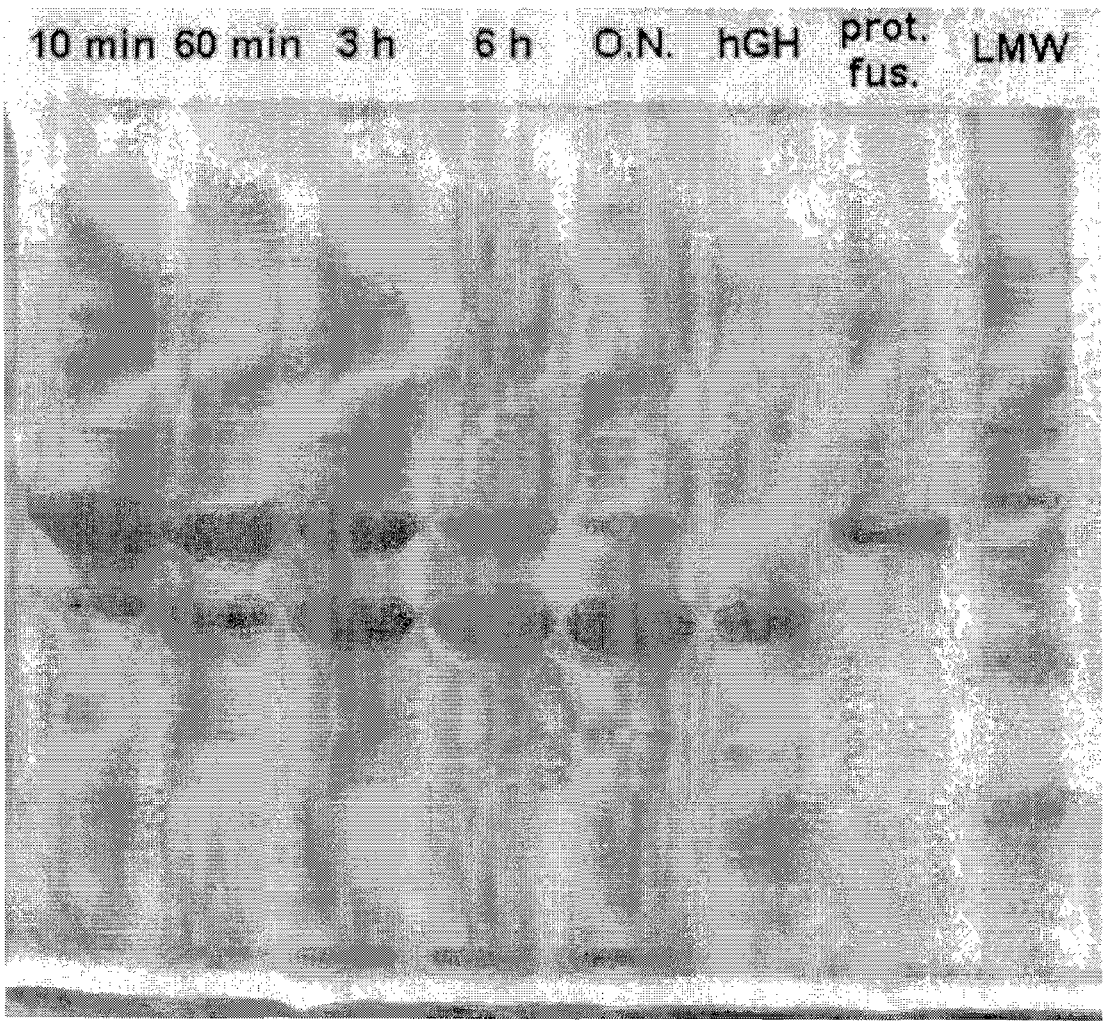
FIG. 7 shows the in vitro digestion profile of a fusion protein obtained with an immobilised ss-Kex1 protease of the present invention that can be re-used in the freeing of the protein of interest from the fusion partner.

The immobilised Kex1 protein was used in the processing of a fusion protein $PNP_{20aa}$-hGH, incubating the latter at 37° C. at a ratio of 10:1 with the immobilised enzyme. Under those conditions, the processing of the protein was continued for a period of from 10 minutes to 15 hours by SDS-PAGE. After 6 hours' incubation, digestion equal to approximately 60% of the fused protein is obtained and almost complete digestion is obtained after 15 hours (FIG. 7). Subsequent re-use of the same preparation of immobilised Kex1 protease under identical operating conditions led to a result substantially identical to the previous result, thus demonstrating that, under the conditions adopted, the immobilised Kex1 protease does not lose activity appreciably even after 30 hours' incubation at 37° C. and can be re-used in the freeing of the protein of interest from the fusion partner.

What is claimed is:

1. A method for making a recombinant peptide or protein comprising:
   (a) producing a fusion protein comprising, at the NH$_2$-terminal end of a peptide or protein of interest, an amino acid sequence containing a dipeptide site hydrolysable by a soluble *Kluyveromyces lactis* Kex1 endoprotease free from its transmembrane domain;
   (b) incubating the fusion protein of step (a) in the presence of a soluble *Kluyveromyces lactis* Kex1 endoprotease consisting of the amino acid sequence set forth as amino acid residues 103 through 600 of SEQ ID NO 3, or amino acid residues 103 through 611 of SEQ ID NO 3; and
   (c) separating and purifying the peptide or protein of interest.

2. The method of claim 1, wherein the hydrolysable dipeptide site is Lys-Arg, Arg-Arg, or Pro-Arg.

3. The method of claim 1, wherein the peptide or protein of interest is a recombinant proteins, selected from the group consisting of peptide hormones, interleukins, interferons, cytokines, growth factors, and fibrinolytic enzymes.

4. The method of claim 1, wherein the soluble *Kluyveromyces lactis* Kex1 endoprotease is immobilised on an insoluble organic or inorganic support.

5. The method of claim 1, wherein the peptide or protein of interest is an enzyme selected from the group consisting of lipases, hydrolases, nucleases, oxidases, and phosphatases.

* * * * *

SEQUENCE LISTING

<160> NUMBER OF SEQ ID NOS: 4

<210> SEQ ID NO 1
<211> LENGTH: 1929
<212> TYPE: DNA
<213> ORGANISM: Kluyveromyces lactis

<400> SEQUENCE: 1

| | | | | | |
|---|---|---|---|---|---|
| atgatcctat | cgtcgcagct | catgctagct | ttaatagcag | tgtcaggata | cggtaaagca | 60 |
| atgcaagttc | ctaaaaaaga | ccacgaaaat | aggcagtatt | ttgcaattga | atcttatgat | 120 |
| gatgtaggta | atctactagc | ggaacacagt | gactggagtt | tcgagcacga | tgttcgaggc | 180 |
| cttgccaatc | actatgtgtt | ctcgaaaccg | ttgcagagtt | tgggtaaacg | agatgcgatt | 240 |
| gacacaggat | attcagaaaa | catcattgat | ttccacgatc | taccccccgt | tcagttacac | 300 |
| aaaagattgc | ctattgggga | ttctagtatg | aacaaatcc | agaacgctag | aattcttttc | 360 |
| aatatttctg | atccattgtt | tgatcagcag | tggcacttga | tcaatccaaa | ctaccctgga | 420 |
| aatgacgtta | acgtaactgg | tttatggaaa | gaaacatca | ctggctatgg | tgtagtggca | 480 |
| gcattggtgg | atgatggatt | ggattatgag | aacgaagatt | taaaagacaa | tttctgtgtt | 540 |
| gaaggttctt | gggattttaa | tgacaacaac | ccattgccga | agccaaggct | aaagatgat | 600 |
| taccatggta | cccgctgcgc | aggtgaaata | gcggctttcc | gtaatgatat | ttgtggggtt | 660 |
| ggtgtcgcct | ataactctaa | ggtatccggt | atcagaattt | tgtcaggcca | gatcacagcc | 720 |
| gaagatgagg | ctgcttcatt | aatttatgga | ctagacgtta | atgatatta | ctcttgctcg | 780 |
| tggggtccat | ctgatgacgg | taaaactatg | caagcgccgg | atacattagt | aaaaaaggca | 840 |
| atcataaaag | gtgtaacaga | aggacgagat | gcaaaaggtg | cactatatgt | atttgcgagt | 900 |
| gggaatggtg | gtatgtttgg | cgacagctgc | aactttgacg | gctacacaaa | ctctatattt | 960 |
| tctatcactg | taggtgccat | tgattggaag | ggcctacatc | ctccatattc | tgaatcatgt | 1020 |
| tctgctgtaa | tggttgttac | ttattcttcg | ggatcaggaa | attacataaa | aacaacagat | 1080 |
| ttagacgaaa | aatgttccaa | tacgcatgga | ggcacttcag | ctgcagctcc | tcttgcagct | 1140 |
| ggtatatata | ctttagtgct | ggaagctaac | ccgaacttaa | catggcgaga | tgtacaatac | 1200 |
| ctctcaatat | tgagctctga | ggaaataaat | ccgcacgatg | gaaagtggca | ggatacagct | 1260 |
| atgggaaagc | gttattctca | cacatatgga | tttggaaaac | ttgatgcata | taacattgtc | 1320 |
| catatggcaa | aaagttggat | caatgtaaac | ccacaaggtt | ggctttacct | tcctacaatc | 1380 |
| gttgaaaaac | agtctatcag | taattcagat | gaagttatag | aatccacagt | ctcagtttct | 1440 |
| gctgaagagt | ttaaacaaaa | taacctaaaa | aggttggaac | atgtcactgt | aactgtcgat | 1500 |
| atagacgcac | cttaccgtgg | acatgtctta | gtagatctaa | tatcgcctga | tggagttaca | 1560 |
| tctaccttag | cgacagctag | acgtttagat | aaaaaccgct | atggttttca | aaattggact | 1620 |
| ttcatgtctg | tcgcgcactg | gggctctagt | ggagttggaa | gctggaaatt | aaaagtaaag | 1680 |
| tctacgcatg | ataatgaaat | tgtaacactc | aaatcttgga | gattaaagat | gtttggagaa | 1740 |
| actatcgatg | caagaaggc | caaagtgata | tcatatggaa | atgacaaaga | ggatgctgaa | 1800 |
| gttaagagta | ccgaatctaa | aaccacaact | cccactgcac | aaacttcgtc | attcacgacg | 1860 |
| acttctggag | aagaaacatc | tggtgcaaat | aagttgcctc | gtcccgaaca | ggctgcccag | 1920 |
| ttatacttg | | | | | | 1929 |

<210> SEQ ID NO 2
<211> LENGTH: 643
<212> TYPE: PRT
<213> ORGANISM: Kluyveromyces lactis

<400> SEQUENCE: 2

```
Met Ile Leu Ser Ser Gln Leu Met Leu Ala Leu Ile Ala Val Ser Gly
1               5                   10                  15

Tyr Gly Lys Ala Met Gln Val Pro Lys Lys Asp His Glu Asn Arg Gln
            20                  25                  30

Tyr Phe Ala Ile Glu Ser Tyr Asp Asp Val Gly Asn Leu Leu Ala Glu
        35                  40                  45

His Ser Asp Trp Ser Phe Glu His Asp Val Arg Gly Leu Ala Asn His
    50                  55                  60

Tyr Val Phe Ser Lys Pro Leu Gln Ser Leu Lys Arg Asp Ala Ile
65                  70                  75                  80

Asp Thr Gly Tyr Ser Glu Asn Ile Ile Asp Phe His Asp Leu Pro Pro
            85                  90                  95

Val Gln Leu His Lys Arg Leu Pro Ile Gly Asp Ser Ser Met Glu Gln
        100                 105                 110

Ile Gln Asn Ala Arg Ile Leu Phe Asn Ile Ser Asp Pro Leu Phe Asp
    115                 120                 125

Gln Gln Trp His Leu Ile Asn Pro Asn Tyr Pro Gly Asn Asp Val Asn
130                 135                 140

Val Thr Gly Leu Trp Lys Glu Asn Ile Thr Gly Tyr Gly Val Val Ala
145                 150                 155                 160

Ala Leu Val Asp Asp Gly Leu Asp Tyr Glu Asn Glu Asp Leu Lys Asp
            165                 170                 175

Asn Phe Cys Val Glu Gly Ser Trp Asp Phe Asn Asp Asn Pro Leu
        180                 185                 190

Pro Lys Pro Arg Leu Lys Asp Asp Tyr His Gly Thr Arg Cys Ala Gly
    195                 200                 205

Glu Ile Ala Ala Phe Arg Asn Asp Ile Cys Gly Val Gly Val Ala Tyr
210                 215                 220

Asn Ser Lys Val Ser Gly Ile Arg Ile Leu Ser Gly Gln Ile Thr Ala
225                 230                 235                 240

Glu Asp Glu Ala Ala Ser Leu Ile Tyr Gly Leu Asp Val Asn Asp Ile
            245                 250                 255

Tyr Ser Cys Ser Trp Gly Pro Ser Asp Asp Gly Lys Thr Met Gln Ala
        260                 265                 270

Pro Asp Thr Leu Val Lys Lys Ala Ile Ile Lys Gly Val Thr Glu Gly
    275                 280                 285

Arg Asp Ala Lys Gly Ala Leu Tyr Val Phe Ala Ser Gly Asn Gly Gly
290                 295                 300

Met Phe Gly Asp Ser Cys Asn Phe Asp Gly Tyr Thr Asn Ser Ile Phe
305                 310                 315                 320

Ser Ile Thr Val Gly Ala Ile Asp Trp Lys Gly Leu His Pro Pro Tyr
            325                 330                 335

Ser Glu Ser Cys Ser Ala Val Met Val Val Thr Tyr Ser Ser Gly Ser
        340                 345                 350

Gly Asn Tyr Ile Lys Thr Thr Asp Leu Asp Glu Lys Cys Ser Asn Thr
    355                 360                 365

His Gly Gly Thr Ser Ala Ala Ala Pro Leu Ala Ala Gly Ile Tyr Thr
370                 375                 380
```

```
Leu Val Leu Glu Ala Asn Pro Asn Leu Thr Trp Arg Asp Val Gln Tyr
385                 390                 395                 400

Leu Ser Ile Leu Ser Ser Glu Glu Ile Asn Pro His Asp Gly Lys Trp
            405                 410                 415

Gln Asp Thr Ala Met Gly Lys Arg Tyr Ser His Thr Tyr Gly Phe Gly
        420                 425                 430

Lys Leu Asp Ala Tyr Asn Ile Val His Met Ala Lys Ser Trp Ile Asn
    435                 440                 445

Val Asn Pro Gln Gly Trp Leu Tyr Leu Pro Thr Ile Val Glu Lys Gln
450                 455                 460

Ser Ile Ser Asn Ser Asp Glu Val Ile Glu Ser Thr Val Ser Val Ser
465                 470                 475                 480

Ala Glu Glu Phe Lys Gln Asn Asn Leu Lys Arg Leu Glu His Val Thr
                485                 490                 495

Val Thr Val Asp Ile Asp Ala Pro Tyr Arg Gly His Val Leu Val Asp
            500                 505                 510

Leu Ile Ser Pro Asp Gly Val Thr Ser Thr Leu Ala Thr Ala Arg Arg
        515                 520                 525

Leu Asp Lys Asn Arg Tyr Gly Phe Gln Asn Trp Thr Phe Met Ser Val
    530                 535                 540

Ala His Trp Gly Ser Ser Gly Val Gly Ser Trp Lys Leu Lys Val Lys
545                 550                 555                 560

Ser Thr His Asp Asn Glu Ile Val Thr Leu Lys Ser Trp Arg Leu Lys
                565                 570                 575

Met Phe Gly Glu Thr Ile Asp Ala Lys Lys Ala Lys Val Ile Ser Tyr
            580                 585                 590

Gly Asn Asp Lys Glu Asp Ala Glu Val Lys Ser Thr Glu Ser Lys Thr
        595                 600                 605

Thr Thr Pro Thr Ala Gln Thr Ser Ser Phe Thr Thr Ser Gly Glu
    610                 615                 620

Glu Thr Ser Gly Ala Asn Lys Leu Pro Arg Pro Glu Gln Ala Ala Gln
625                 630                 635                 640

Leu Tyr Leu

<210> SEQ ID NO 3
<211> LENGTH: 700
<212> TYPE: PRT
<213> ORGANISM: Kluyveromyces lactis

<400> SEQUENCE: 3

Met Ile Leu Ser Ser Gln Leu Met Leu Ala Leu Ile Ala Val Ser Gly
1               5                   10                  15

Tyr Gly Lys Ala Met Gln Val Pro Lys Lys Asp His Glu Asn Arg Gln
            20                  25                  30

Tyr Phe Ala Ile Glu Ser Tyr Asp Asp Val Gly Asn Leu Leu Ala Glu
        35                  40                  45

His Ser Asp Trp Ser Phe Glu His Asp Val Arg Gly Leu Ala Asn His
    50                  55                  60

Tyr Val Phe Ser Lys Pro Leu Gln Ser Leu Gly Lys Arg Asp Ala Ile
65                  70                  75                  80

Asp Thr Gly Tyr Ser Glu Asn Ile Ile Asp Phe His Asp Leu Pro Pro
                85                  90                  95

Val Gln Leu His Lys Arg Leu Pro Ile Gly Asp Ser Ser Met Glu Gln
            100                 105                 110
```

-continued

```
Ile Gln Asn Ala Arg Ile Leu Phe Asn Ile Ser Asp Pro Leu Phe Asp
        115                 120                 125

Gln Gln Trp His Leu Ile Asn Pro Asn Tyr Pro Gly Asn Asp Val Asn
        130                 135                 140

Val Thr Gly Leu Trp Lys Glu Asn Ile Thr Gly Tyr Gly Val Val Ala
145                 150                 155                 160

Ala Leu Val Asp Asp Gly Leu Asp Tyr Glu Asn Glu Asp Leu Lys Asp
                165                 170                 175

Asn Phe Cys Val Glu Gly Ser Trp Asp Phe Asn Asp Asn Asn Pro Leu
            180                 185                 190

Pro Lys Pro Arg Leu Lys Asp Asp Tyr His Gly Thr Arg Cys Ala Gly
        195                 200                 205

Glu Ile Ala Ala Phe Arg Asn Asp Ile Cys Gly Val Gly Val Ala Tyr
    210                 215                 220

Asn Ser Lys Val Ser Gly Ile Arg Ile Leu Ser Gly Gln Ile Thr Ala
225                 230                 235                 240

Glu Asp Glu Ala Ala Ser Leu Ile Tyr Gly Leu Asp Val Asn Asp Ile
                245                 250                 255

Tyr Ser Cys Ser Trp Gly Pro Ser Asp Asp Gly Lys Thr Met Gln Ala
            260                 265                 270

Pro Asp Thr Leu Val Lys Lys Ala Ile Ile Lys Gly Val Thr Glu Gly
        275                 280                 285

Arg Asp Ala Lys Gly Ala Leu Tyr Val Phe Ala Ser Gly Asn Gly Gly
    290                 295                 300

Met Phe Gly Asp Ser Cys Asn Phe Asp Gly Tyr Thr Asn Ser Ile Phe
305                 310                 315                 320

Ser Ile Thr Val Gly Ala Ile Asp Trp Lys Gly Leu His Pro Pro Tyr
                325                 330                 335

Ser Glu Ser Cys Ser Ala Val Met Val Val Thr Tyr Ser Ser Gly Ser
            340                 345                 350

Gly Asn Tyr Ile Lys Thr Thr Asp Leu Asp Glu Lys Cys Ser Asn Thr
        355                 360                 365

His Gly Gly Thr Ser Ala Ala Ala Pro Leu Ala Ala Gly Ile Tyr Thr
    370                 375                 380

Leu Val Leu Glu Ala Asn Pro Asn Leu Thr Trp Arg Asp Val Gln Tyr
385                 390                 395                 400

Leu Ser Ile Leu Ser Ser Glu Glu Ile Asn Pro His Asp Gly Lys Trp
                405                 410                 415

Gln Asp Thr Ala Met Gly Lys Arg Tyr Ser His Thr Tyr Gly Phe Gly
            420                 425                 430

Lys Leu Asp Ala Tyr Asn Ile Val His Met Ala Lys Ser Trp Ile Asn
        435                 440                 445

Val Asn Pro Gln Gly Trp Leu Tyr Leu Pro Thr Ile Val Glu Lys Gln
    450                 455                 460

Ser Ile Ser Asn Ser Asp Glu Val Ile Glu Ser Thr Val Ser Val Ser
465                 470                 475                 480

Ala Glu Glu Phe Lys Gln Asn Asn Leu Lys Arg Leu Glu His Val Thr
                485                 490                 495

Val Thr Val Asp Ile Asp Ala Pro Tyr Arg Gly His Val Leu Val Asp
            500                 505                 510

Leu Ile Ser Pro Asp Gly Val Thr Ser Thr Leu Ala Thr Ala Arg Arg
        515                 520                 525

Leu Asp Lys Asn Arg Tyr Gly Phe Gln Asn Trp Thr Phe Met Ser Val
```

```
                    530             535             540
Ala His Trp Gly Ser Ser Gly Val Gly Ser Trp Lys Leu Lys Val Lys
545                     550                     555                 560

Ser Thr His Asp Asn Glu Ile Val Thr Leu Lys Ser Trp Arg Leu Lys
                565                     570                 575

Met Phe Gly Glu Thr Ile Asp Ala Lys Lys Ala Lys Val Ile Ser Tyr
            580                     585                 590

Gly Asn Asp Lys Glu Asp Ala Glu Val Lys Ser Thr Glu Ser Lys Thr
                595                     600                 605

Thr Thr Pro Thr Ala Gln Thr Ser Ser Phe Thr Thr Ser Gly Glu
        610                     615                 620

Glu Thr Ser Gly Ala Asn Lys Leu Pro Arg Pro Glu Gln Ala Ala Gln
625                     630                     635                 640

Leu Tyr Leu Ala Ile Phe Val Ile Gly Ala Val Ile Ile Ile Tyr
                    645                     650                 655

Tyr Leu Phe Phe Leu Lys Ser Arg Arg Ile Ile Arg Arg Ser Arg Ala
                660                     665                 670

Glu Ala Tyr Glu Phe Asp Ile Ile Asp Thr Asp Ser Glu Tyr Asp Ser
            675                     680                 685

Ser Ile Asn Lys Leu Gln Ser Leu Tyr Leu Val Lys
        690                     695                 700

<210> SEQ ID NO 4
<211> LENGTH: 814
<212> TYPE: PRT
<213> ORGANISM: Saccharomyces cerevisiae

<400> SEQUENCE: 4

Met Lys Val Arg Lys Tyr Ile Thr Leu Cys Phe Trp Trp Ala Phe Ser
1               5                   10                  15

Thr Ser Ala Leu Val Ser Ser Gln Gln Ile Pro Leu Lys Asp His Thr
            20                  25                  30

Ser Arg Gln Tyr Phe Ala Val Glu Ser Asn Glu Thr Leu Ser Arg Leu
        35                  40                  45

Glu Glu Met His Pro Asn Trp Lys Tyr Glu His Asp Val Arg Gly Leu
50                  55                  60

Pro Asn His Tyr Val Phe Ser Lys Glu Leu Leu Lys Leu Gly Lys Arg
65                  70                  75                  80

Ser Ser Leu Glu Glu Leu Gln Gly Asp Asn Asn Asp His Ile Leu Ser
                85                  90                  95

Val His Asp Leu Phe Pro Arg Asn Asp Leu Phe Lys Arg Leu Pro Val
            100                 105                 110

Pro Ala Pro Pro Met Asp Ser Ser Leu Leu Pro Val Lys Glu Ala Glu
        115                 120                 125

Asp Lys Leu Ser Ile Asn Asp Pro Leu Phe Glu Arg Gln Trp His Leu
130                 135                 140

Val Asn Pro Ser Phe Pro Gly Ser Asp Ile Asn Val Leu Asp Leu Trp
145                 150                 155                 160

Tyr Asn Asn Ile Thr Gly Ala Gly Val Val Ala Ala Ile Val Asp Asp
                165                 170                 175

Gly Leu Asp Tyr Glu Asn Glu Asp Leu Lys Asp Asn Phe Cys Ala Glu
            180                 185                 190

Gly Ser Trp Asp Phe Asn Asp Asn Thr Asn Leu Pro Lys Pro Arg Leu
        195                 200                 205
```

-continued

```
Ser Asp Asp Tyr His Gly Thr Arg Cys Ala Gly Glu Ile Ala Ala Lys
210                 215                 220
Lys Gly Asn Asn Phe Cys Gly Val Gly Val Gly Tyr Asn Ala Lys Ile
225                 230                 235                 240
Ser Gly Ile Arg Ile Leu Ser Gly Asp Ile Thr Thr Glu Asp Glu Ala
            245                 250                 255
Ala Ser Leu Ile Tyr Gly Leu Asp Val Asn Asp Ile Tyr Ser Cys Ser
            260                 265                 270
Trp Gly Pro Ala Asp Asp Gly Arg His Leu Gln Gly Pro Ser Asp Leu
            275                 280                 285
Val Lys Lys Ala Leu Val Lys Gly Val Thr Glu Gly Arg Asp Ser Lys
290                 295                 300
Gly Ala Ile Tyr Val Phe Ala Ser Gly Asn Gly Gly Thr Arg Gly Asp
305                 310                 315                 320
Asn Cys Asn Tyr Asp Gly Tyr Thr Asn Ser Ile Tyr Ser Ile Thr Ile
                325                 330                 335
Gly Ala Ile Asp His Lys Asp Leu His Pro Pro Tyr Ser Glu Gly Cys
                340                 345                 350
Ser Ala Val Met Ala Val Thr Tyr Ser Ser Gly Ser Gly Glu Tyr Ile
            355                 360                 365
His Ser Ser Asp Ile Asn Gly Arg Cys Ser Asn Ser His Gly Gly Thr
370                 375                 380
Ser Ala Ala Ala Pro Leu Ala Ala Gly Val Tyr Thr Leu Leu Leu Glu
385                 390                 395                 400
Ala Asn Pro Asn Leu Thr Trp Arg Asp Val Gln Tyr Leu Ser Ile Leu
                405                 410                 415
Ser Ala Val Gly Leu Glu Lys Asn Ala Asp Gly Asp Trp Arg Asp Ser
            420                 425                 430
Ala Met Gly Lys Lys Tyr Ser His Arg Tyr Gly Phe Gly Lys Ile Asp
            435                 440                 445
Ala His Lys Leu Ile Glu Met Ser Lys Thr Trp Glu Asn Val Asn Ala
450                 455                 460
Gln Thr Trp Phe Tyr Leu Pro Thr Leu Tyr Val Ser Gln Ser Thr Asn
465                 470                 475                 480
Ser Thr Glu Glu Thr Leu Glu Ser Val Ile Thr Ile Ser Glu Lys Ser
                485                 490                 495
Leu Gln Asp Ala Asn Phe Lys Arg Ile Glu His Val Thr Val Thr Val
            500                 505                 510
Asp Ile Asp Thr Glu Ile Arg Gly Thr Thr Val Asp Leu Ile Ser
            515                 520                 525
Pro Ala Gly Ile Ile Ser Asn Leu Gly Val Val Arg Pro Arg Asp Val
530                 535                 540
Ser Ser Glu Gly Phe Lys Asp Trp Thr Phe Met Ser Val Ala His Trp
545                 550                 555                 560
Gly Glu Asn Gly Val Gly Asp Trp Lys Ile Lys Val Lys Thr Thr Glu
                565                 570                 575
Asn Gly His Arg Ile Asp Phe His Ser Trp Arg Leu Lys Leu Phe Gly
            580                 585                 590
Glu Ser Ile Asp Ser Ser Lys Thr Glu Thr Phe Val Phe Gly Asn Asp
            595                 600                 605
Lys Glu Glu Val Glu Pro Ala Ala Thr Glu Ser Thr Val Ser Gln Tyr
610                 615                 620
Ser Ala Ser Ser Thr Ser Ile Ser Ile Ser Ala Thr Ser Thr Ser Ser
```

```
-continued 625                   630                   635                   640
Ile Ser Ile Gly Val Glu Thr Ser Ala Ile Pro Gln Thr Thr Thr Ala
                645                   650                   655

Ser Thr Asp Pro Asp Ser Asp Pro Asn Thr Pro Lys Lys Leu Ser Ser
            660                   665                   670

Pro Arg Gln Ala Met His Tyr Phe Leu Thr Ile Phe Leu Ile Gly Ala
            675                   680                   685

Thr Phe Leu Val Leu Tyr Phe Met Phe Phe Met Lys Ser Arg Arg Arg
            690                   695                   700

Ile Arg Arg Ser Arg Ala Glu Thr Tyr Glu Phe Asp Ile Ile Asp Thr
705                   710                   715                   720

Asp Ser Glu Tyr Asp Ser Thr Leu Asp Asn Gly Thr Ser Gly Ile Thr
                725                   730                   735

Glu Pro Glu Glu Val Glu Asp Phe Asp Phe Asp Leu Ser Asp Glu Asp
            740                   745                   750

His Leu Ala Ser Leu Ser Ser Ser Glu Asn Gly Asp Ala Glu His Thr
            755                   760                   765

Ile Asp Ser Val Leu Thr Asn Glu Asn Pro Phe Ser Asp Pro Ile Lys
    770                   775                   780

Gln Lys Phe Pro Asn Asp Ala Asn Ala Glu Ser Ala Ser Asn Lys Leu
785                   790                   795                   800

Gln Glu Leu Gln Pro Asp Val Pro Pro Ser Ser Gly Arg Ser
                805                   810
```